United States Patent [19]
Briggs

[11] 3,993,222
[45] Nov. 23, 1976

[54] VARIABLE-VOLUME DISPOSABLE APPLIANCE

[76] Inventor: David Briggs, 200 Hamburg 6, Geffckenstr. 6 Germany

[22] Filed: Aug. 19, 1975

[21] Appl. No.: 605,828

[30] Foreign Application Priority Data
Aug. 21, 1974 Germany............................ 2439975

[52] U.S. Cl................................. 222/107; 222/215
[51] Int. Cl.²........................................ B65D 35/04
[58] Field of Search.................... 222/107, 215, 104

[56] References Cited
UNITED STATES PATENTS

| | | | |
|---|---|---|---|
| 1,377,113 | 5/1921 | Boyle............................. | 222/107 X |
| 1,623,107 | 4/1927 | Goodykoontz..................... | 222/107 |
| 2,723,779 | 11/1955 | Parker et al. ....................... | 222/104 |
| 2,942,760 | 6/1960 | Schneider........................... | 222/107 |
| 3,463,358 | 8/1969 | Wenzler.......................... | 222/107 X |
| 3,595,441 | 7/1971 | Grosjean.......................... | 222/107 |

*Primary Examiner*—Allen N. Knowles
*Assistant Examiner*—Hadd Lane
*Attorney, Agent, or Firm*—Michael J. Striker

[57] ABSTRACT

The appliance has a container that is formed of folded sheet material which bounds an internal chamber and includes a plurality of walls. The container is deformable between a first condition in which the volume of the internal chamber is at a minimum and a second condition in which the volume of the chamber is at a maximum. The container is capable of aspirating a medium when deformed from the first towards the second condition and of expelling a medium when deformed from the second toward the first condition.

14 Claims, 19 Drawing Figures

VARIABLE-VOLUME DISPOSABLE APPLIANCE

BACKGROUND OF THE INVENTION

The present invention relates to a medical appliance in general, and more particularly to a variable-volume medical appliance. Still more particularly, the invention relates to a medical appliance having a variable volume and permitting the aspiration into and the expulsion from an internal chamber of the appliance, of a fluid medium. The appliance is advantageously disposable, i.e., intended for a single use.

Variable-volume disposable medical appliances of the type with which the present invention is concerned serve to draw fluids into an internal chamber and/or to expel fluids therefrom. Conventionally, this is accomplished with syringes, of which the needle is inserted into the tissue or into a blood vessel of a human or animal organism and either suction is produced to withdraw a quantity of fluid or pressure is produced to expel from the interior chamber of the syringe a fluid which is to be injected into the organism, for example a medication or the like. The conventional syringes can be used many times. However, between each use a conventional syringe must be sterilized. This often creates problems in terms of time, facilities or even adequacy of the sterilization. The prior art has therefore proposed a piston-type syringe which is intended for a single use, i.e., it is to be used once and then disposed of. These, however, are relatively expensive and other less expensive solutions are therefore desirable in this field. Moreover, syringes of the conventional type --whether they be reusable or of the disposable type-- create problems if they are to be used by a patient himself, as is often the case, for example with diabetics who must carry out their own injections. Such persons must draw up a sufficient quantity of medication into the syringe from a supply, and being unskilled have often been found to either exceed the required dosage or not to reach it at all.

Another type of prior art syringe, which was conceived to be disposable and does not make use of a piston structure, provides a cylinder which is hollow and from whose interior a fluid is expelled by exerting pressure upon the exterior of the cylinder to compress the same in transverse direction. The disadvantage encountered in this prior-art syringe or medical appliance resides in the fact that although it is capable of ejecting a fluid and injecting it into a human or animal organism or the like, it is incapable of aspirating a fluid, for example of drawing blood from a blood vessel. Therefore, in the case of an intended intravenous injection, this type of appliance cannot be used to determine, prior to injection of the contents, whether the needle is actually properly located in a vein, which is a test conventionally done by drawing some blood out of the vein into the syringe and, when it is found that such blood is in fact present and that therefore the needle is in fact located in the vein as required, to inject the contents of the syringe. This test is, however, also necessary in almost all other instances, e.g., also in the intra-muscular and the subcutaneous types of injection.

In these latter two types of injection, a medication is injected not into a blood vessel but into a body tissue and, since many medications intended for subcutaneous or intramuscular application can lead to disastrous effects when they are erroneously injected intravenously, it is mandatory to ascertain, e.g., by aspiration, that the tip of the injection needle is not in a blood vessel. When the needle is not located in a blood vessel, no blood appears in the syringe when suction is applied.

The significance of this test for the correct position of the injection needle is illustrated by the cases of certain diabetics who, subsequent to erroneously intravenous self-injection of insulin, which should have been injected subcutaneously, came to their deaths in a state of hypoglycemia. The test for the correct position of the injection needle by aspiration is conventional clinical procedure and it can be performed with piston-type syringes; however, it requires a change of hand position between aspiration and injection; this manipulation, especially when it is performed by laymen, can alter the originally correct position of the injection needle. Moreover, laymen often neglect to perform the aspiration test, and until now no syringe has become known which allows injection only after this test has been performed.

SUMMARY OF THE INVENTION

Accordingly, it is an object of this invention to provide an improved medical appliance of the type in question which avoids the disadvantages outlined above with respect to the prior art.

More particularly, it is an object of this invention to provide such an improved medical appliance which is of such a construction that it can serve as a package for a medium that is to be injected, and that it can serve both to aspirate a medium in the interior of the appliance--e.g., blood to determine the penetration of a blood vessel--as well as to thereupon inject the contents of the appliance into whatever tissue or blood vessel has been penetrated.

An additional object of the invention is to provide such a medical appliance, which is of the variable-volume type and is advantageously disposable, which can be used simply and with complete safety even by laymen.

Another object of the invention is to provide such a medical appliance which permits a control of the position of the tip of the inserted needle, i.e., which permits due to the possibility of aspiration to check whether the needle has been properly inserted into a blood vessel, tissue or the like.

In keeping with these objects, and with others which will become apparent hereafter, one feature of the invention resides in a variable-volume disposable medical appliance that comprises a container formed of folded sheet material which bounds an internal chamber and includes a plurality of walls. The container is deformable between a first condition in which the volume of the internal chamber is at a minimum and a second condition in which the volume of the internal chamber is at a maximum. The container is capable of aspirating a medium when deformed from the first toward the second condition so that its internal volume increases, and of expelling a medium when deformed from the second to the first condition so that its internal volume decreases.

A medical appliance of this type is inexpensive to produce and can be factory pre-filled with the desired type and quantity of medium to be injected.

In particular, the container is deformed from the first towards its second condition to such an extent as is necessary to accommodate the desired quantity of medium with which the container is to be pre-filled. This quantity of the medium can subsequently be ejected completely and without any residue from the container, by deforming the container in direction towards its first condition, i.e., more or less flattening the container. On the other hand, if and when it is necessary to aspirate a fluid into the interior of the container, such as to control whether the tip of the injection needle is located in a blood vessel, the container is further deformed towards its second condition, thereby further increasing its volume beyond that which is already filled with a pre-selected quantity of medium to be injected, and this creates suction in the interior of the container and suffices to aspirate blood or the like into it, thus affording the user a check concerning the proper insertion of the needle. When it has been determined that the needle is indeed properly inserted, pressure is exerted upon the container in a sense deforming it again from the second towards the first condition, thereby reducing the volumetric content of the container and causing the ejection of the medium contained therein, including any blood that may have been previously aspirated.

According to a currently preferred embodiment the container is of such a construction that when pressure is exerted upon it it will deform in such a way that its volumetric content will first increase for aspirating purposes, and when the pressure is further exerted in the same sense and direction as before, the volumetric content of the container will then decrease so that the contents of the container will be expelled i.e., this embodiment has three distinguished positions, a first position with minimum volume, a second, intermediate position with maximum volume and a third position, which again has minimum volume, but is geometrically different from the first position. Due to the construction of the container, absolutely none of the medium in the container--except perhaps for a film on the interior container surfaces--will remain so that the proper pre-selected quantity of medium is injected.

The novel features which are considered characteristic of the invention are set forth in particular in the appended claims. The invention itself, however, both as to its construction and its method of operation, will be best understood from the following description of preferred embodiments when read in connection with the accompanying drawing.

DESCRIPTION OF THE PREFERRED EMBODIMENTS

Referring firstly to the embodiment illustrated in FIGS. 1-8 of the drawing, it will be seen that this embodiment utilizes a container 2 which is made of sheet material and can be folded together and apart to thereby decrease and increase its volumetric content, respectively. It should be understood that the container 2 will be provided with a suitable outlet and, at this outlet, with a suitable connection so that an injection needle 1 (shown in the embodiment of FIG. 9 but omitted in FIGS. 1-8) can be connected to this outlet. The outlet and the means for connecting the needle 1 to the same have not been illustrated since these measures are of course fully well known both from reusable and disposable syringes of the prior art. Also, details of hollow injection needles used in conjunction with syringes are known from the prior art and require no discussion, especially as the needles do not form a part of the invention.

Figure 1:
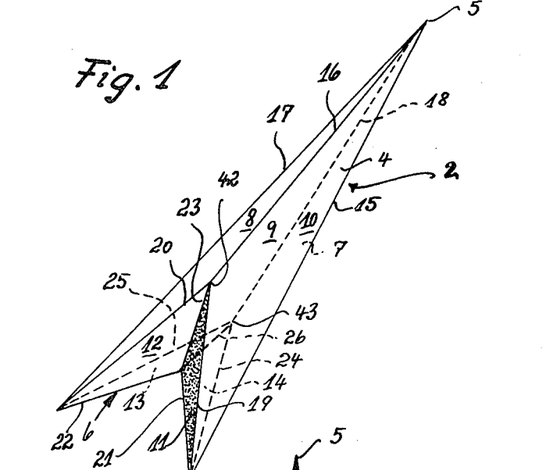
FIG. 1 is a perspective view illustrating an appliance according to the present invention in its folded-apart condition in which its interior has the maximum volumetric content possible.
Figure 2:
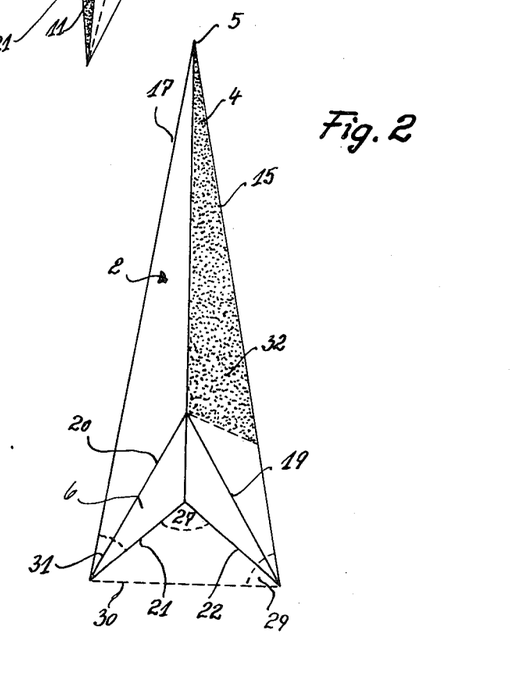
FIG. 2 is a top-plan view of the appliance in FIG. 1, showing the latter in folded-together position in which the interior has the minimum volumetric content.
Figure 3:
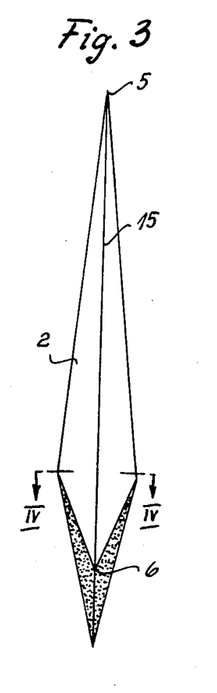
FIG. 3 is a top-plan view showing the appliance of FIGS. 1 and 2 in partially folded-apart condition.
Figure 4:
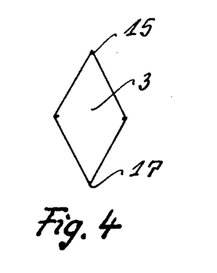
FIG. 4 is a diagrammatic cross-section on line IV—IV of FIG. 3 to illustrate the cross-sectional contour of the appliance when it is in the position of FIG. 3.
Figure 5:
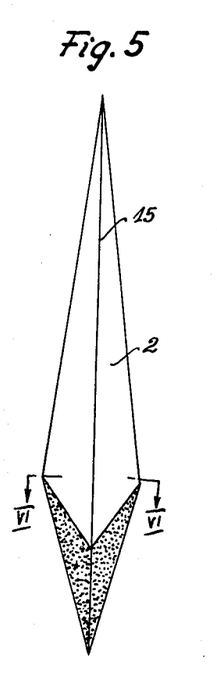
FIG. 5 shows the appliance of FIG. 3 in completely folded-apart condition in which its interior has the maximum possible volumetric content.
Figure 6:
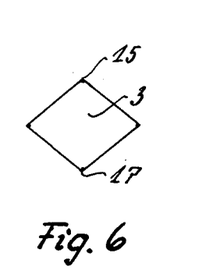
FIG. 6 is a diagrammatic section taken on line VI—VI of FIG. 5.
Figure 7:
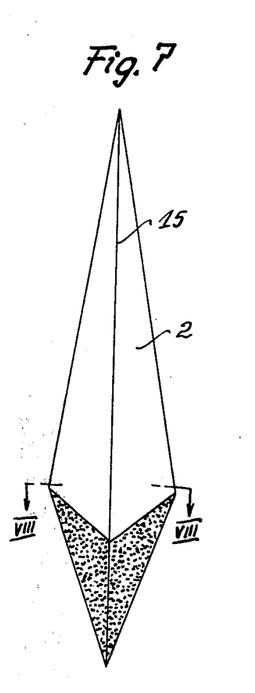
FIG. 7 is a top-plan view of the appliance in FIGS. 3 and 5, but showing it in again partially folded condition.
Figure 8:
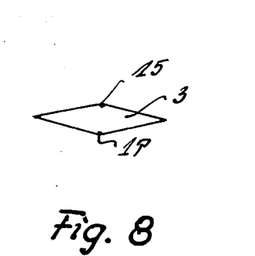
FIG. 8 is a diagrammatic section taken on line VIII—VIII of FIG. 7.

As FIGS. 1-8 show, the container 2 in this embodiment is folded, being of sheet material, and surrounding an interior or internal chamber 3 whose volumetric content can be increased and decreased, as a comparison of FIGS. 4, 6 and 8 will subsequently illustrate. The sheet material may be plastics, the kind of which depends upon the kind of medicine which is to be filled into the internal chamber 3, because the container 2 is not to be damaged and the medicine is not to be influenced by the sheet material. The conatiner 2 has an elongated body 4 which is of arrowhead-shaped or pyramidal configuration and provided with a tip 5 and an end or bottom closure 6. The body 4 is composed of four wall portions 7, 8, 9 and 10 each of which also cooperates with a wall portion 11, 12, 13 or 14 of the end closure 6. The wall portions 7–10 join one another again along respective fold lines 15, 16, 17 and 18 which extend longitudinally of the body 4 and along which the adjacent wall portions can fold or flex relative to one another. Similarly, the wall portions 11–14 of the bottom closure or end closure 6 can be folded relative to one another along fold lines 19, 20, 21, 22, 23, 24, 25 and 26.

Two of the longitudinally extending fold lines, namely in this embodiment the fold lines 15 and 17, are also constructed as seams, the body 4 being composed of two sheet material portions one of which has the wall portions 7 and 8 and the other of which has the wall portions 9 and 10. These two sheet material portions are connected with one another along the seams which coincide with the fold lines 15 and 17. Similarly, the seams 21 and 22 of the bottom closure 6 connect the two parts 11–12 and 13–14 with one another, of which the bottom closure 6 is composed. The other fold lines 16, 18, 19, 20, 23, 24, 25 and 26, are formed in the material of the wall portions 7–10 and 11–14, respectively, by appropriate folding thereof, embossing or the like.

The particular construction of the end closure 6 in the embodiment of FIGS. 1—8 makes it possible to fold the container 2 in such a manner that it becomes completely flat (compare FIG. 2) so that the inner surfaces of the corresponding wall portions 11–14 are in immediate abutment with one another, without any possibility that any space might remain between the cooperating wall portions 12–13 or 11–14, respectively. For this purpose, the folds 21, 22 converge in arrowhead shape towards one another when the body 2 or container 2 is folded together, forming an angle 27. Similarly, the fold lines 19–20 converge in arrowhead-shaped configuration in direction towards the tip 5 and form with one another a more acute angle 28. The fold lines 21, 22 bisect a base angle 29 which is formed by an imaginary base line 30 and the respective longitudinally extending folds 15 and 17. The base line 30, incidentally, connects the outermost points of the end closure 6, where the longitudinally extending seams 15, 17 intersect with the fold lines 21, 22 of the end closure 6.

In addition, the end closure 6 is so constructed that the fold lines 19, 20 which include the angle 28, bisect an angle 31 which is included between the fold lines 21 and 17. In this manner, the mutually corresponding wall portions 11 and 12 are symmetrical relative to one another and thus can overlie one another in folded condition in a coextensive relationship. Thus, when the container 2 is folded together as shown in FIGS. 7 and 8 the wall portions 11 and 12 abut one another with their external surfaces, depending upon the direction of folding, so that the inner surfaces of the wall portions 7-10 engage them from the inside, i.e., the inner surfaces of the wall portions 11 and 14 are superimposed upon the wall portions 10 and 7, respectively.

As a general rule, the container 2 of the present invention as shown in FIGS. 1-8, will be pre-filled prior to sale with a medium to be injected, for example with a quantity of medicine. However, it will be only partially filled, i.e., the maximum possible volumetric content of the chamber 3 will not be utilized for filling with medicine. When subsequently the container 2 is to be used then a needle 1 will be connected to it, for example via a connecting arrangement which may be located at the tip 5, and as a result of the connection of the needle an opening located at the connecting arrangement will be opened to establish communication between the chamber 3 and the interior of the needle. Or, on the other hand, the syringe may be sold already equipped with an irremovable injection needle protected by a closure which at the same time serves as a seal to help prevent inadvertent ejection or contamination of the contents. When the needle 1 is then inserted, for example into a blood vessel, and it is desired to determine whether a proper insertion into a blood vessel has in fact taken place, the user will exert pressure upon the container 2 at the fold lines 15, 17. In other words: in FIG. 4 the user will press against fold line 15 in a downward direction in the Figure, and upon the fold line 17 in an upward direction so that the fold lines 15 and 17 move towards one another as the container 2 becomes deformed. This increases the volumetric content of the chamber 3, as is clear from a comparison of FIGS. 3–4 with FIGS. 5–6. As a result of this increase in the volumetric content of the chamber 3, suction is created in the interior of the chamber 3 and this suffices to draw blood or the like through the needle 1 (which is inserted into a blood vessel or the like) into the chamber 3. The material of which the container 2 is made should of course be transparent or at least translucent, or at least one of the wall portions or part of one of the wall portions should have this characteristic, so that the user can observe the entry of the blood into the chamber 3 and satisfy himself that the tip of the needle has been properly inserted into a blood vessel. Thereupon, the user continues to exert pressure upon the fold lines 15, 17 in the same direction as before. This causes a collapse of the container 2 and results in a decrease of the volumetric content of the chamber 3, as a comparison of FIGS. 6 and 8 clearly indicates, FIG. 8 showing the decreased volumetric content. During this collapse from the volumetric content in FIG. 6 to that in FIG. 8, the medication and blood or other aspirated medium in the interior of the chamber 3 will be expelled through the needle and injected into the blood vessel into which the needle is inserted.

To assure that when the container 2 is in the folded-together condition shown in FIGS. 7 and 8, there will be zero or substantially zero volumetric content to the interior of the container, the inner surfaces of the wall portions 7–10 and 8–9 may be provided with cover layers 32 for the purpose of compensating for thickness differentials that may result from the fact that seams are created by connecting the two portions forming the container 2 along the fold lines 15 and 17, respectively and because without these cover layers the wall portions 8–10 and 7–9 would actually be separated by the combined thicknesses of wall portions 11–12 and 13–14, respectively. This assures that the inner surfaces of the wall portions 8–10 and the wall portion 7–9 respectively, are in immediately abutment with one another and that the volumetric content in the interior of the container 2 will be at or near zero. The material of the layers 32 may be of the same kind as that of the container 2. It must be guaranteed, that the medicine is not influenced by the container 2 and the layers 32.

Figures 9, 10:
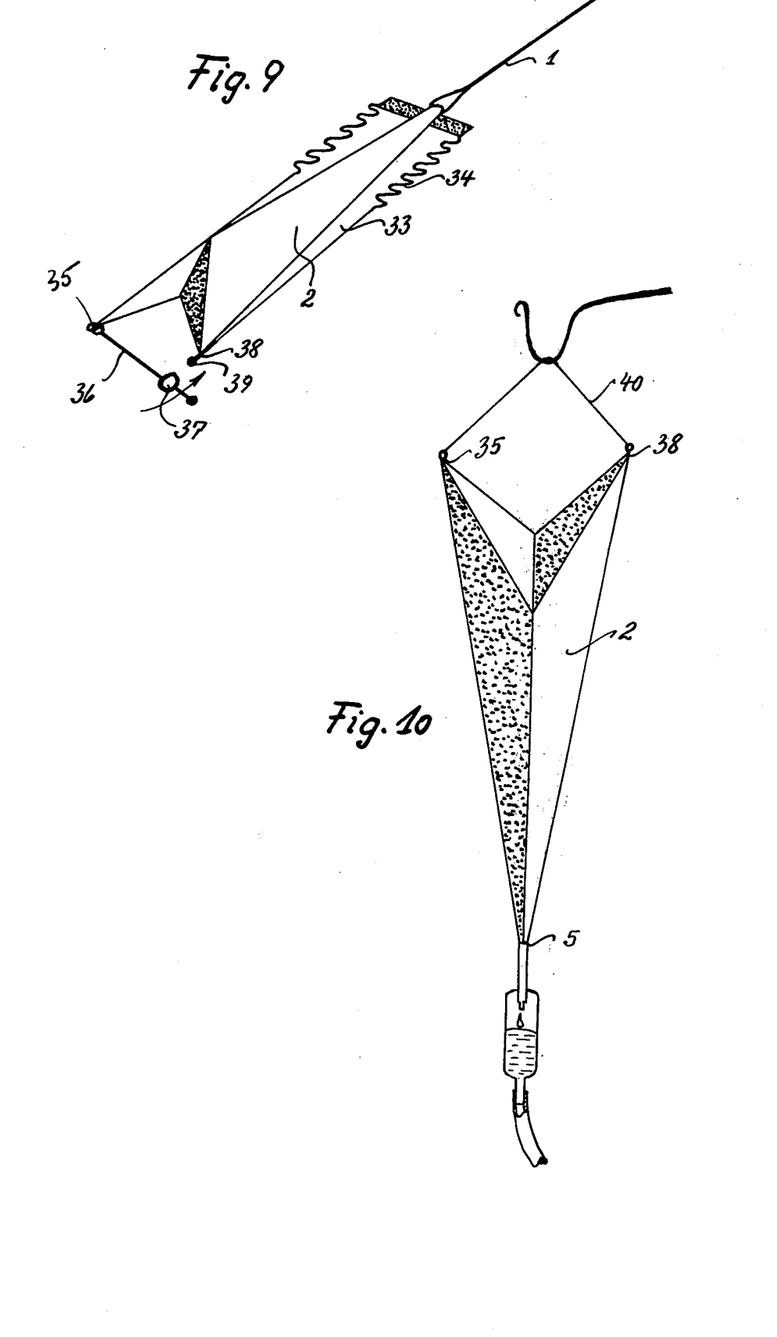
FIG. 9 is a perspective view of an appliance according to a further embodiment of the invention.
FIG. 10 is a perspective view showing still an additional embodiment of the invention.

FIGS. 9 and 10 show that supporting edge portions 33 may be provided extending along the seams 15, 17 for the purpose of stabilizing the container 2 in a certain folded-apart condition. These portions 33 may additionally be provided with indentations or the like 34 (see FIG. 9) which may serve as a further indication of the magnitude of the dose of medicine contained in the container 2, for example a predetermined number of insulin units. This may be an indication in addition to a printed or otherwise provided inidcia furnishing the same information.

Figures 17, 18:
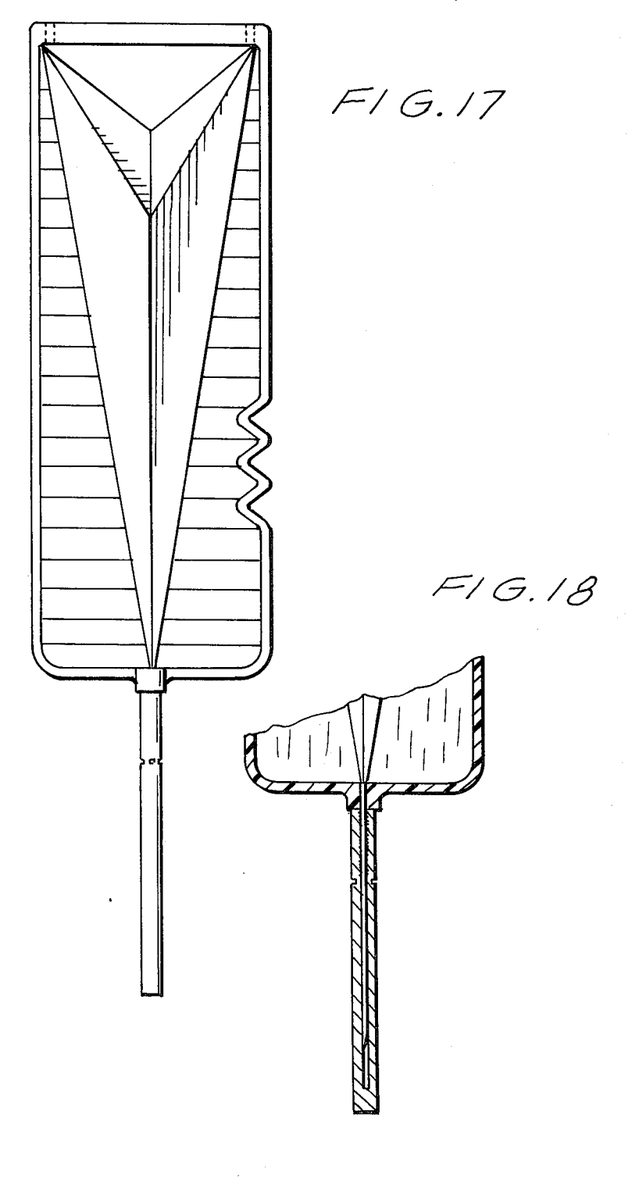
FIG. 17 is an axial section through yet a further embodiment.
FIG. 18 shows a detail of FIG. 17 in a sectional view--.

To prevent unintentional collapsing of the container 2 under circumstances where this is not desired, one of the rearwardly extending edges of the container 2, namely the edge 35 in FIG. 9, may be provided with a latch 36 having an eyelet 37 therein, and the eyelet 37 may be pushed onto a pin 39 extending from another rearwardly extending edge 38 of the container 2, so that the relatively rigid latch member 36 prevents undesired collapsing of the container 2. The latch member may also be constructed in such a way that it must be torn off or broken before the container can be used. This is shown in FIGS. 17 and 18.

The appliance of the present invention can also serve for infusion purposes. In this case it is suspended on a hanger, for example the illustrated hook in FIG. 10, by means of a supporting arrangement 40 such as a wire, thread or the like, that is connected to the end portions 35 and 38. Under the influence of its own weight and the weight of its contents, the container 2 tends to pull downwardly and this in turn tends to move the end portions 35 and 38 towards one another, thus collapsing the container and permitting an infusion to be carried out with it as shown in FIG. 10.

If an infusion under increased pressure is desired, then a weight 41 may be suspended (for example in the manner shown in FIG. 11) from the container 2, for the purpose of making the end portions 35 and 38 move towards one another under the influence of the weight 41 and to expel the contents.

FIG. 12 shows an embodiment which is analogous to the embodiment of FIGS. 1–8, or that of FIGS. 9 and 10, except that the container 2--which in the embodiment of FIG. 12 is again to be used for infusion purposes--is urged towards collapsed (and thus expelling) position by an elastomeric element 42 which is connected to the end portions 35 and 38 and urges the same towards one another, thus expelling the contents.

Figures 11, 12, 13A, 13B:
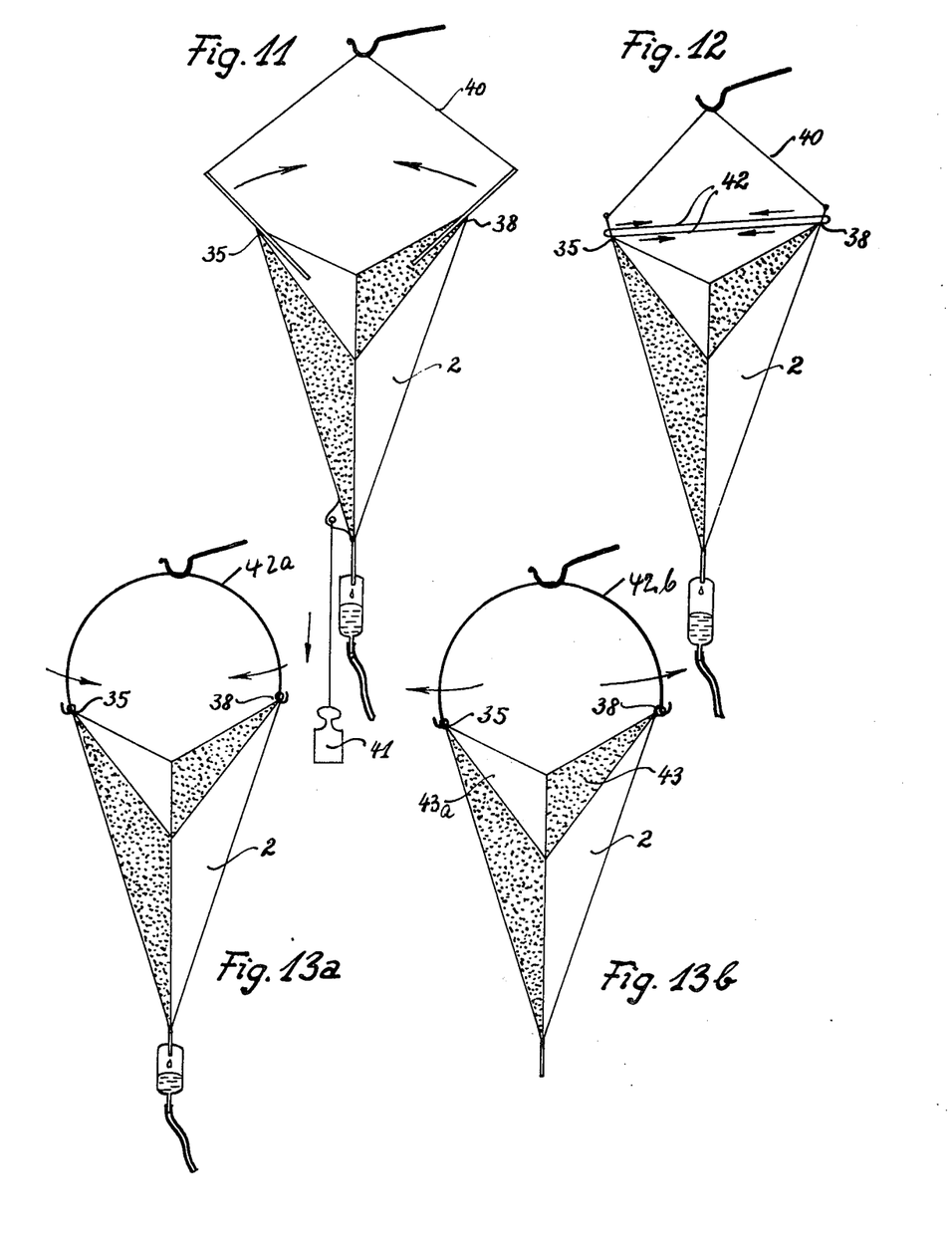
FIG. 11 is a view analogous to FIG. 10, showing another embodiment of the invention.
FIG. 12 is a view similar to FIG. 11 showing yet a further embodiment of the invention.
FIG. 13a is a view similar to FIG. 12 but illustrating another embodiment of the invention.
FIG. 13b is a view similar to FIG. 13a illustrating a somewhat modified embodiment of the invention.

FIG. 13a shows an embodiment similar to FIG. 12, except that the elastomeric element 42, such as a rubber band or the like, is here replaced with a spring steel hoop or bracket 42a which exerts inward pressure upon the end portions 35 and 38 to which it is connected, tending to collapse the container 2 and expel its contents. An air-vent is not required.

If it is desired to use the container 2 for aspirating a liquid from an organism or the like, in a gradual manner and without requiring manual operation, then the container 2 can again be suspended as shown in FIG. 13b where, as in FIG. 13a, the hoop 42b serves the same purpose as the suspending arrangement 40 of FIG. 12. In this case, however, the hoop 42b will be of the type that tends to expand, i.e., to exert outward pressure as indicated by the arrows, and to urge the end portions 35 and 38 to which it is connected apart from one another. This tends to increase the volumetric content of the container 2 and to aspirate liquid from whatever source into which the needle provided on the container (not shown) is inserted.

Figure 14:
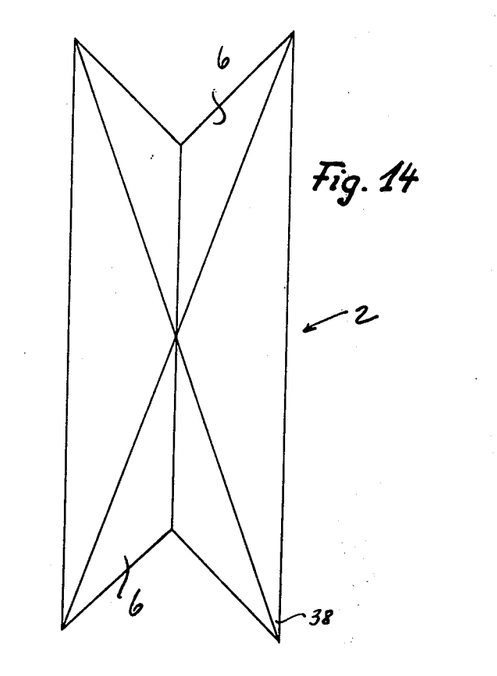
FIG. 14 is a top-plan view illustrating diagrammatically a further embodiment of the invention.
Figure 15:
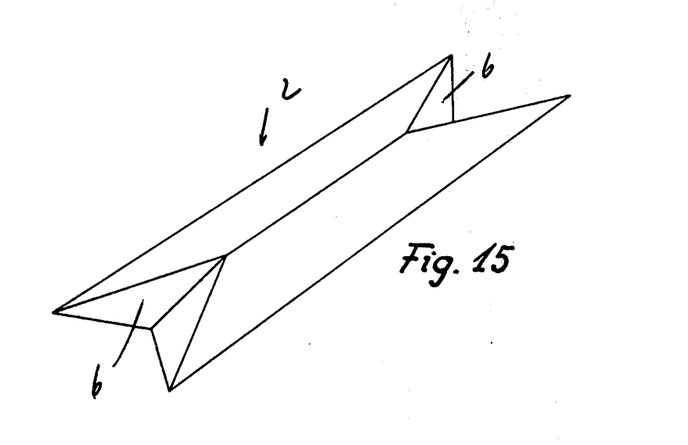
FIG. 15 is a perspective view of an appliance according to still another embodiment of the invention.

FIGS. 14 and 15 show two embodiments of further containers of the present invention, the containers again being identified with reference numeral 2. In these two embodiments, however, the containers are provided with end closures 6 at both of their opposite ends. In all other respects, the two embodiments in FIGS. 14 and 15 are analogous to the one in FIGS. 1–8. One of the tips in each of the embodiments of FIGS. 14 and 15, for instance the tip 38 in FIG. 14, may be provided with an opening and with a connector (not shown) to which an injection needle may be connected in the usual manner. The embodiments of FIGS. 14 and 15 are particularly advantageous if a relatively large quantity of medicine is to be injected.

Figure 16:
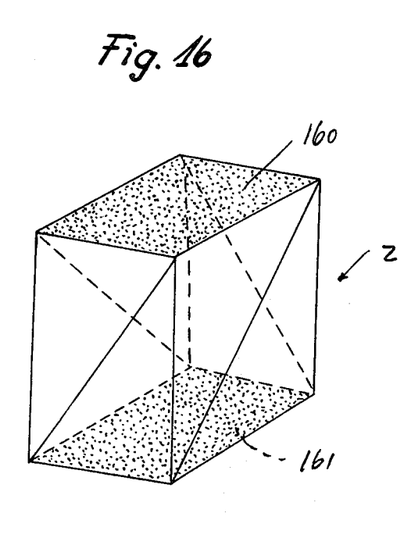
FIG. 16 is a perspecitve view of yet an additional embodiment of the invention.

Finally, FIG. 16 is illustrative of the possibility that the container 2 of the invention may also have a prismatic shape, having top and bottom walls 160 and 161, respectively, which may be triangular or may be of a different polygonal outline. In FIG. 16 the top wall 160 and the bottom wall 161 are of rectangular outline. The fold lines are illustrated in FIG. 16 but not provided with separate reference numerals. By twisting the top wall 160 and the bottom wall 161 in mutually opposite directions they will move closer towards one another, i.e., the top wall 160 will move down and the bottom wall 161 will move up. This decreases the volumetric content in the interior of the container 2 in FIG. 16 and ejects any liquid contained therein through an appropriate outlet (not illustrated). Conversely, if the walls 160, 161 are already located closer together than illustrated in FIG. 16, and they are twisted relative to one another so that they move apart to the position shown in FIG. 16, the volumetric content of the container 2 will be increased and the container 2 will be made to aspirate blood or the like through a needle connected with it and inserted into a blood vessel. In this cases the container 2 is only partially filled with medicine, so that blood may enter it, whereas the container 2 is twisted into the position shown in FIG. 16. After aspirating in that way the whole content of the container 2 is injected into the blood vessel.

The containers according to the present invention can be produced in any of the conventional container-manufacturing ways that is suitable for this purpose. They can be welded (e.g., heat welded if they are of plastic) or adhesively bonded. They can also be produced by casting or injection molding if they are made of synthetic plastic material.

While the invention has been described and illustrated and embodied in a variable-volume disposable medical appliance, it is not intended to be limited to the details shown, since various modifications and structrual changes may be made without departing in any way from the spirit of the present invention.

It will be understood that each of the elements described above, or two or more together, may also find a useful application in other types of apparatus differing from the types described above. In this connection, it will be especially understood that the container 2 can be used according to the invention for packaging and dispensing viscous products such as, for example, tooth paste, ketchup and motor oil.

Without further analysis, the forgoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended:

1. A variable-volume disposable appliance comprising a container formed of a plurality of walls which are separated from each other by fold lines, said walls constituting means bounding an internal chamber which is deformable between a first position in which the volume of said internal chamber is at a minimum and in which said container is substantially flat and a second position in which the volume of said internal chamber is at a maximum and yet a third position in which the volume of said internal chamber is again at a minimum, said container being consecutively deformable from said first to said second and third positions by means of a force applied in only one direction, said container being capable of aspirating a medium when deformed either from said first or third position towards said second position and of expelling a medium when deformed from second position towards either of said first or third positions, in which different ones of said walls abut one another with their respective inner surfaces, the aforesaid deformation causing bending of the material only at said fold lines.

2. An appliance as defined in claim 1, said container being of substantially pyramidal configuration and having four longitudinal fold lines converging towards its apex, said longitudinal fold lines separating respective ones of said walls which abut one another with their inner surfaces when said container is in said first and third positions, said container having an outlet at the apex end and having a closure at the end opposite the apex, said closure being composed of four wall portions which abut one another in overlying relationship when said container is in said first and third positions, said wall portions of said end closure being separated from each other by a first pair of mutually inclined end fold lines forming a bottom fold of said end closure and the latter being provided with two additional pairs of end fold lines which extends towards one another from respective corners of said end closure at angles which are steeper than the angle included between the end fold lines of said first pair.

3. An appliance as defined in claim 2, wherein each of said fold lines of said first pair bisects the angle included by each of said longitudinal fold lines with an imaginary line connecting said corners when said container is in said first position; and wherein each end fold line of said additional pairs bisects the angle included between said end fold lines of said first pair and said two longitudinal fold lines when said container is in said first position.

4. An appliance as defined in claim 2, said two longitudinal fold lines being provided with outwardly extending margines which are elastically connected with each other at the apex of the container, said margins serving to stabilize said container in a desired volumetric condition.

5. An appliance as defined in claim 4, said margins being provided with indentations which serve as an indication in code form as to the contents of said container.

6. An appliance as defined in claim 1, said container being of substantially prismatic configuration and having a number of fold lines which is a multiple of two and which extend parallel to each other when said container is in said first and third positions, said longitudinal fold lines separating respective ones of said walls which abut one another when said container is in said first and said third position, said container having end closure at both ends.

7. An appliance as defined in claim 1, said walls having inner surfaces; and further comprising cover layers provided on said inner surfaces and in direct abutment with one another when said container is in said third position.

8. An appliance as defined in claim 1, comprising means acting upon said container so as to cause the same to undergo deformation from aid second towards said first or third positions and to exert expelling pressure upon the medium in said container.

9. An appliance as defined in claim 1, comprising means acting upon said container so as to cause the same to undergo deformation from either of said first or third positions towards said second position and to cause aspiration of medium into said container by means of suction.

10. An appliance as defined in claim 1, said container beng substantially of prismatic configuration in said second position and having a plurality of longitudinal folds and further having end closures, said end closures each consisting of one wall, said end closure being twistable relative to one another in substantially parallel planes to deform said container between said first, second and third positions thereof.

11. A variable-volume disposable medial appliance, comprising an infusion container formed of folded sheet material constituting means which bounds an internal chamber and includes a plurality of walls, said container being deformable between a first condition in which the volume of said internal chamber is at a minimum and a second condition in which the volume of said chamber is at a maximum, said container being capable of aspirating a medium when deformed from said first towards second condition and of expelling a medium when deformed from said second toward said first first condition; means for suspending said container so that the latter can assume said first condition under its own weight; said container having an end closure formed with corners which move toward one another when said container undergoes deformation from said second towards said first condition, said means for suspending being connected to said corners; and weight means acting upon said container so as to cause the same to undergo deformation from said second towards said first condition and to exert constant expelling pressure upon medium in said chamber.

12. A variable-volume disposable medical appliance, comprising an infusion container formed of folded sheet material which bounds an internal chamber and includes a plurality of walls, said container being deformable between a first condition in which the volume of said internal chamber is at a minimum and a second condition in which the volume of said internal chamber is at a maximum, said container being capable of aspirating a medium when deformed from said first toward said second condition and of expelling a medium when deformed from said second toward said first condition; means for suspending said container so that the latter can assume said first condition under its own weight; said containing having an end closure formed with corners which move towards one another when said container undergoes deformation from said second towards said first condition; and a contractile elastomeric element connected to said corners to urge the same to move towards one another.

13. A variable-volume disposable medical appliance, comprising an infusion container formed of folded sheet material which bounds an internal chamber and includes a plurality of walls, said container being deformable between a first condition in which a volume of internal chamber is at a minimum and a second condition in which the volume of said internal chamber is at a maximum, said container being capable of aspirating a medium when deformed from said first toward said second condition and of expelling a medium when deformed from said second toward said first condition; means for suspending said container so that the latter can assume said first condition under its own weight; said container having an end closure formed with corners which are moved towards one another when said container undergoes deformation from said second towards said first condition; and a spring bracket connected to said corners to urge the same to move towards one another.

14. A variable-volume disposable medical appliance, comprising an infusion container formed of folded sheet material which bounds an internal chamber and includes a plurality of walls, said container being deformable between a first condition in which the volume of said internal chamber is at a minimum and a second condition in which the volume of said internal chamber is at a maximum, said container being capable of aspirating a medium when deformed from said first toward said second condition and of expelling a medium when deformed from said second toward said first condition; means for suspending said container so that the latter can assume said first condition under its own weight; said container having an end closure formed with corners which move towards one another when said container undergoes deformation from said second towards said first condition; and a spring bracket connected to said corners and urging the same away from one another.

* * * * *